US011251998B2

(12) United States Patent
Biber et al.

(10) Patent No.: US 11,251,998 B2
(45) Date of Patent: Feb. 15, 2022

(54) PILOT TONE DEVICE, MAGNETIC RESONANCE TOMOGRAPHY SYSTEM WITH PILOT TONE DEVICE, AND OPERATING METHOD

(71) Applicant: Siemens Healthcare GmbH, Erlangen (DE)

(72) Inventors: Stephan Biber, Erlangen (DE); David Grodzki, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/900,982

(22) Filed: Jun. 14, 2020

(65) Prior Publication Data
US 2020/0396112 A1 Dec. 17, 2020

(30) Foreign Application Priority Data

Jun. 13, 2019 (DE) .......................... 102019208583.0

(51) Int. Cl.
H04L 27/12 (2006.01)
A61B 5/055 (2006.01)
G01R 33/36 (2006.01)
G01R 33/56 (2006.01)

(52) U.S. Cl.
CPC ............. *H04L 27/12* (2013.01); *A61B 5/055* (2013.01); *G01R 33/3621* (2013.01); *G01R 33/5608* (2013.01)

(58) Field of Classification Search
CPC ..... H04L 27/12; A61B 5/055; G01R 33/3621; G01R 33/5608
See application file for complete search history.

(56) References Cited

U.S. PATENT DOCUMENTS

| 2009/0082683 | A1* | 3/2009 | Mustafa | G01R 33/28 600/509 |
| 2014/0070807 | A1 | 3/2014 | Biber | |
| 2015/0207653 | A1 | 7/2015 | Oppelt | |
| 2016/0245888 | A1 | 8/2016 | Bollenbeck | |
| 2017/0160367 | A1 | 6/2017 | Schröter | |
| 2018/0081030 | A1* | 3/2018 | McMahon | G01S 13/87 |
| 2018/0353139 | A1* | 12/2018 | Speier | A61B 5/7292 |
| 2018/0353140 | A1* | 12/2018 | Speier | G01R 33/56308 |
| 2019/0298217 | A1* | 10/2019 | Speier | A61B 5/0536 |

(Continued)

FOREIGN PATENT DOCUMENTS

DE 102012216292 A1 5/2014
DE 102015203385 A1 8/2016
(Continued)

OTHER PUBLICATIONS

German Office Action for German Application No. 10 2019 208 583.0 dated Apr. 18, 2020.
(Continued)

*Primary Examiner* — G.M. A Hyder
(74) *Attorney, Agent, or Firm* — Lempia Summerfield Katz LLC

(57) ABSTRACT

A pilot tone device for acquiring physiological data of a patient and a magnetic resonance tomography system with a corresponding pilot tone device are provided. The pilot tone device has a pilot tone transmitter that is designed to transmit a pilot tone in an ISM band.

8 Claims, 1 Drawing Sheet

(56) References Cited

U.S. PATENT DOCUMENTS

| | | | | |
|---|---|---|---|---|
| 2019/0377051 A1* | 12/2019 | Bacher | ................... | G16H 40/63 |
| 2020/0022607 A1* | 1/2020 | Pratt | ..................... | A61B 5/6892 |
| 2020/0110145 A1* | 4/2020 | Zeller | ................... | A61B 5/113 |
| 2020/0166597 A1* | 5/2020 | Speier | ................... | H04B 13/005 |
| 2020/0249292 A1* | 8/2020 | Biber | ................. | G01R 33/4818 |
| 2020/0333419 A1* | 10/2020 | Zhang | ................. | A61B 5/7285 |
| 2020/0367765 A1* | 11/2020 | Bacher | ................. | A61B 5/7214 |
| 2020/0375463 A1* | 12/2020 | Hess | ................... | A61B 5/7289 |

FOREIGN PATENT DOCUMENTS

| | | | |
|---|---|---|---|
| DE | 102015224158 A1 | 6/2017 | |
| EP | 3467531 A1 | 4/2019 | |
| WO | WO2015150953 A1 | 10/2015 | |

OTHER PUBLICATIONS

Lenk, Mary Claire. Respiratory Motion Tracking in Magnetic Resonance Imaging with Pilot Tone Technology. Diss. The Ohio State University, 2018. pp. 1-72.

Schroeder, Lea, et al. "A novel method for contact-free cardiac synchronization using the pilot tone navigator." Proceedings of the 24th Annual Meeting of ISMRM, Singapore. 2016. Abstract 0410.

* cited by examiner

PILOT TONE DEVICE, MAGNETIC RESONANCE TOMOGRAPHY SYSTEM WITH PILOT TONE DEVICE, AND OPERATING METHOD

This application claims the benefit of German Patent Application No. DE 10 2019 208 583.0, filed on Jun. 13, 2019, which is hereby incorporated by reference in its entirety.

BACKGROUND

The present embodiments relate to a pilot tone device with a pilot tone transmitter and a pilot tone receiver.

Pilot tone devices transmit a weak electromagnetic alternating field, which interacts with the body of a patient as a result of damping, reflection, and/or interference. As a result, amplitude and/or phase are changed. A time variation occurs with movements in the body of the patient, and therefore, internal movement as a result of breathing, heartbeat, or digestion may also be acquired without putting stress on the patient as a result of internal sensors or those attached to the skin.

Magnetic resonance tomography systems are imaging devices that, in order to image an object under examination, align nuclear spins of the object under examination with a strong external magnetic field, and use an alternating magnetic field to excite the nuclear spins to precess about this alignment. The precession or return of the spins from this excited state into a state with less energy in turn generates, as a response, an alternating magnetic field that is received via antennas.

With the aid of magnetic gradient fields, a spatial encoding is impressed onto the signals, which then permits an assignment of the received signal to a volume element. The received signal is then evaluated, and a three-dimensional imaging representation of the object under examination is provided.

Depending on the pulse sequence used, also referred to as sequence, the image acquisition in a magnetic resonance tomography system requires a number of milliseconds up to seconds. A longer acquisition time may result in minimal noise artifacts. The image acquisition may therefore be started in each case at the start of a phase, in which the body remains relatively still, in order to avoid motion artifacts due to a movement during the image acquisition. Unavoidable movements are, for example, breathing and heartbeat. However, a phase of relative rest (e.g., after breathing out or a contraction of the cardiac muscle) also follows a phase with movements. An image acquisition in this phase is to expect a relatively long-time frame with few movements so that the best measurement results are to be expected.

It is fundamentally already known to acquire the movements using mechanical sensors or using electrodes that measure the excitation potential of the muscles, for example.

The publication DE 10 2015 203 385 describes a basic method of acquiring movements using a radio frequency signal. The signal is, for example, permanently acquired in a patient recording of a magnetic resonance tomography system, and signal changes as a result of movements (e.g., as a result of changing interferences or damping) are evaluated. A movement of the patient, caused by breathing or heartbeat, may then be identified from certain patterns of this signal.

The publication WO 2015/150953 A1 discloses a transmitter for emitting a synchronization signal, the two antennas of which are arranged at the ends of a patient leadthrough. A pilot tone may also be emitted as, for example, a synchronization signal.

The publication DE 10 2015 224 158 describes a transmitter for pilot tone navigation in a magnetic resonance tomography system and a method for identifying a movement of a patient. The transmitter has a power supply and an antenna. The transmitter is configured to transmit a pilot tone signal via the antenna. The transmitter also has a decoupling element in order to protect the transmitter power from signals that the antenna receives during magnetic resonance tomography in excitation pulses of the magnetic resonance tomography system. In the method, movement-dependent changes to the pilot tone signal of the transmitter are identified by a controller of the magnetic resonance tomography system.

SUMMARY AND DESCRIPTION

The scope of the present invention is defined solely by the appended claims and is not affected to any degree by the statements within this summary.

The present embodiments may obviate one or more of the drawbacks or limitations in the related art. For example, the application of a pilot tone signal is improved.

The pilot tone device is configured to acquire physiological data. This may be that a signal that changes with physiological processes in the body of the patient is generated with the pilot tone device so that the processes may be detected by a receiver. The receiver may be a receiver of the pilot tone device. In one embodiment, the pilot tone signal may be received by a receiver of a medical imaging device (e.g., a receiver of a magnetic resonance tomography system). The pilot tone device has, for example, a pilot tone transmitter configured to transmit a pilot tone in an ISM band. ISM bands are radio frequency bands that are released in regulatory terms for industrial, scientific, and medical applications. For example, no other applications that may be disturbed by the emitted signals are provided in these frequency bands. Higher transmit powers without shielding measures are therefore also permitted in these bands. A higher disturbance level is, however, to be expected as a result of concurring applications. An exemplary frequency band, in which large powers may also be permitted, lies between 26.9 and 27.3 MHz. Other frequency bands of this type lie between 6.7 MHz and 6.8 MHz, 13.5 MHz and 13.6 MHz, 40.6 MHz and 40.7 MHz, as well as 433.0 MHz and 434.8 MHz.

A pilot tone application in an ISM band enables an application without complicated shielding measures and thus, for example, also mobile applications in patient couches, etc.

In one embodiment, the pilot tone device has a receiver for receiving the pilot tone. A signal link, via which the pilot tone transmitter obtains an item of information about a disturbance level at the frequency of the pilot tone, exists between the receiver and the pilot tone transmitter. This may specify a disturbance signal level or a signal-to-noise ratio, for example. The pilot tone transmitter is configured, for example, to set a transmit power of the pilot tone as a function of the disturbance level at a frequency of the pilot tone. For example, the pilot tone device may be configured to increase an amplification of the pilot tone signal to be transmitted with an increasing disturbance level so that a constant and adequate signal-to-noise ratio may be achieved.

A disturbance signal-dependent power control enables an adequate signal level for a reliable recording of physiological data in the undisturbed environment and also a minimum radiation in an undisturbed environment.

In one possible embodiment, the pilot tone transmitter of the pilot tone device has a modulator. The modulator is configured to modulate the pilot tone with a correlation pattern. A simple amplitude or frequency modulation with a pure tone of a specific frequency may be provided, but more complex types of modulation such as QPSK or QAM with bit sequences such as pseudo random sequences may also be provided. Even spread spectrum modulation with a signal level below the noise limit may be provided. A receiver has a complementary correlator that is configured to filter the received pilot tone signal based on the modulation. Depending on the type of modulation, a corresponding narrow band filter or decoder may be possible for the selected type of modulation, or an autocorrelator may be provided for identifying the pseudo bit sequence.

The modulation of the pilot tone with a uniquely identifiable pattern allows for the disturbance signals to be differentiated and/or separated, and thus, also enables operation in an undisturbed frequency band without shielding.

In one embodiment, a magnetic resonance tomography system includes a pilot tone device. The magnetic resonance tomography system is configured to use a magnetic resonance signal in an ISM band for imaging. With respect to the ISM bands, reference is made to the preceding embodiments. The fact that the static magnetic field B0 of a field magnet for nuclear spin alignment has a strength at which the Larmor frequency of the nuclear spins to be imaged comes to rest in an ISM band, and thus, magnetic alternating fields generated thereupon to excite the nuclear spins have a frequency in an ISM band, is considered, for example, to be utilization of the imaging.

A Larmor frequency in an ISM band provides that higher limit values apply to a radiation of the excitation pulses in the room, and it is therefore possible to entirely dispense with a radio frequency shielding chamber for the magnetic resonance tomography system or for this to be omitted essentially more easily.

In one possible embodiment of the magnetic resonance tomography system, the pilot tone transmitter and the magnetic resonance tomography system are configured to generate pilot tone and the magnetic resonance signal in different ISM bands in each case. ISM bands with in each case disjointed frequency ranges are considered to be different ISM bands. For example, the Larmor frequency may lie between 26.9 and 27.3 MHz, and the pilot tone may have a frequency of 6.7 MHZ and 6.8 MHz.

By using different ISM frequency bands for pilot tone and magnetic resonance signal, separation of the signals is simpler. For example, the receiver for the pilot tone may be provided with simpler filters. At the same time, protective measures for pilot tone transmitter and pilot tone receiver against the high amplitudes of the excitation pulse are to be embodied more easily.

In another embodiment of the magnetic resonance tomography system, the pilot tone transmitter and the magnetic resonance tomography system are configured to generate pilot tone and the magnetic resonance signal in the same ISM band, where the pilot tone signal lies outside of the bandwidth of the magnetic resonance signal. In one embodiment, the pilot tone signal and the frequency of the magnetic resonance signal lie between 26.9 and 27.3 MHz. The frequency range may be that the bandwidth of the magnetic resonance signal, for example, in which, as a function of the frequency, an amplitude of the magnetic resonance signal drops by less than 3 dB, 6 dB or 12 dB compared with a maximum amplitude. The magnetic resonance signal may lie in a frequency range between 27.0 MHz and 27.3 MHz, for example, and the pilot tone signal is at 26.9 MHz.

When the same ISM band is used, a shared receiver may receive and evaluate the pilot tone signal and the magnetic resonance signal, and a separate pilot tone receiver may be dispensed with.

In one embodiment of the magnetic resonance tomography system, the magnetic resonance tomography system has a receiver for the magnetic resonance signal. The receiver has a signal connection with the pilot tone transmitter. The pilot tone transmitter is configured to transmit a reference pilot tone signal via the signal link. In this regard, a signal is considered to be a reference pilot tone signal that specifies the properties of the pilot tone signal without disturbance signals and/or interaction with the patient.

This may include amplitude, phase, and/or modulation, for example. In the simplest case, a signal may be a signal that is fed to a radio frequency output stage of the pilot tone transmitter and is fed to the receiver as a signal link via a shielded line. A data flow with a digitalized pilot tone signal, to which the input signal is fed to the radio frequency output stage, may also be provided. Digital parameters, which are used to generate the pilot tone signal, such as a frequency specification, an amplitude specification, a phase specification, and/or a modulation signal such as a pseudo random integer sequence, may also be possible.

The receiver is configured to suppress a portion of the pilot tone in a received magnetic resonance signal as a function of the reference pilot tone signal. In the simplest case, with a known phase relationship and amplitude ratio between the pilot tone reference signal and pilot tone signal received by the receiver, by inverting the amplitude or a phase displacement by 180 degrees and the same amplitude sum by summation, the portion of the pilot tone signal may be reduced in the received magnetic resonance signal. The portion may also be minimized by varying the cited parameters by an optimization method such as LSR. A modulation (e.g., with the pseudo random integer sequence) facilitates a determination of the optimal parameters using auto correlation.

Disturbance to the imaging by the pilot tone signal may be minimized by actively suppressing the disturbance of the pilot tone signal in the receiver of the magnetic resonance tomography system, even if the frequency ranges of the pilot tone signal and magnetic resonance tomography system overlap partially.

DETAILED DESCRIPTION

Figure 1:
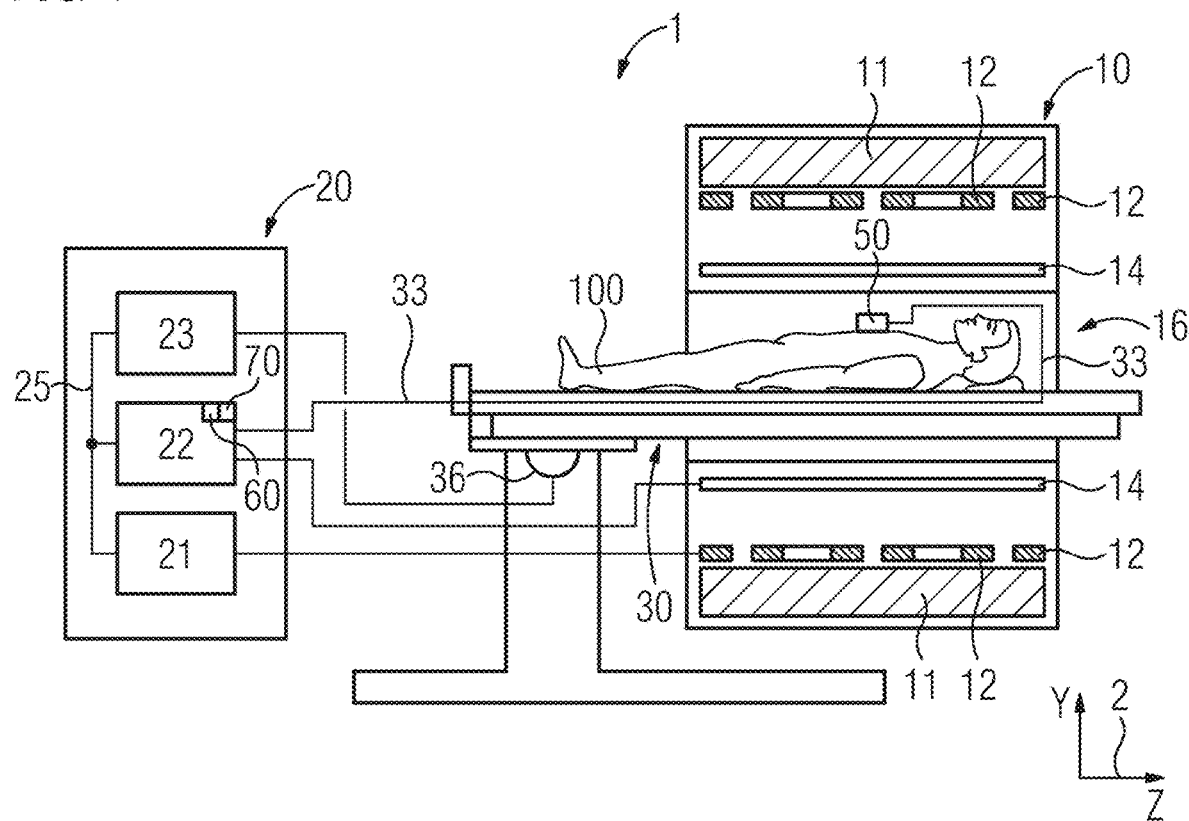
FIG. 1 shows a schematic display of a magnetic resonance tomography system with an embodiment of a pilot tone device and a pilot tone receiver.

FIG. 1 shows a schematic display of an embodiment of a magnetic resonance tomography system 1. The magnetic resonance tomography system 1 includes a pilot tone device with a pilot tone transmitter 60 and a pilot tone receiver 70.

The magnet unit 10 has a field magnet 11 that generates a static magnetic field B0 for aligning nuclear spins of test specimens or the patient 100 in a recording area. The recording area is characterized by an extremely homogenous static magnetic field B0, where the homogeneity relates, for example, to the magnetic field strength or a sum. The recording area is almost conical and arranged in a patient tunnel 16 that extends in a longitudinal direction 2 through the magnet unit 10. A patient couch 30 may be moved in the patient tunnel 16 by the moving unit 36. The field magnet 11 may be a superconducting magnet that may provide magnetic fields having a magnetic flux density of up to 3 T or even higher. For lower field strengths, however, it is also possible to utilize permanent magnets or electromagnets having normally conductive coils.

The magnet unit 10 further includes gradient coils 12 that are configured, for spatial differentiation of the acquired imaging regions in the examination volume, to overlay variable magnetic fields onto the magnetic field B0 in three spatial directions. The gradient coils 12 are typically coils made of normally conducting wires that may generate mutually orthogonal fields in the examination volume.

The magnet unit 10 likewise has a body coil 14 configured to radiate into the examination volume a radio frequency signal supplied via a signal line, and to receive resonance signals emitted by the patient 100 and to output the resonance signals via a signal line.

A control unit 20 (e.g., a controller) supplies the magnet unit 10 with the various signals for the gradient coils 12 and the body coil 14 and evaluates the signals received.

Thus, the control unit 20 has a gradient control 21 that is configured to provide the gradient coils 12 with variable currents via supply lines. The variable currents provide the desired gradient fields in the examination volume on a temporally coordinated basis.

The control unit 20 has a radio frequency unit 22 that is configured to generate a radio frequency pulse with a predetermined temporal sequence, amplitude, and spectral power distribution for excitation of a magnetic resonance of the nuclear spin in the patient 100. Thereby, pulse power levels in the region of kilowatts may be achieved. The excitation pulses may be radiated into the patient 100 via the body coil 14 or also via a local transmitting antenna.

A controller 23 communicates with the gradient control 21 and the radio frequency unit 22 via a signal bus 25.

A local coil 50 is arranged on the patient 100 and is connected via a connecting line 33 with the radio frequency unit 22 and a corresponding receiver.

The radio frequency unit 22 has a pilot tone transmitter 60. The pilot tone transmitter 60 has a signal connection with the local coil 50, which has a transmitting antenna for emitting the pilot tone signal. In one embodiment, a separate transmitting antenna for the pilot tone signal is arranged in the patient tunnel 16 or on the patient 100. In one embodiment, the pilot tone transmitter 60 is arranged in the local coil 50.

The radio frequency unit 22 has a pilot tone receiver 70. The pilot tone receiver 70 has a signal connection with the local coil 50, which has a receiving antenna for receiving the pilot tone signal. In one embodiment, a separate receiving antenna for the pilot tone signal is arranged in the patient tunnel 16 or on the patient 100. The pilot tone receiver 70 may also use one or more antenna coils of the local coils, which are provided to receive the magnetic resonance signal at least if the pilot tone signal and the magnetic resonance signal are in the same ISM band. In one embodiment, the pilot tone receiver 70 may be identical to the receivers for the magnetic resonance signal, and only some additional processing steps in the form of filters or algorithms may be applied to the signal of the antenna coils in order to extract the pilot tone signal. In one embodiment, the pilot tone receiver 70 may be arranged in the local coil 50.

Figure 2:
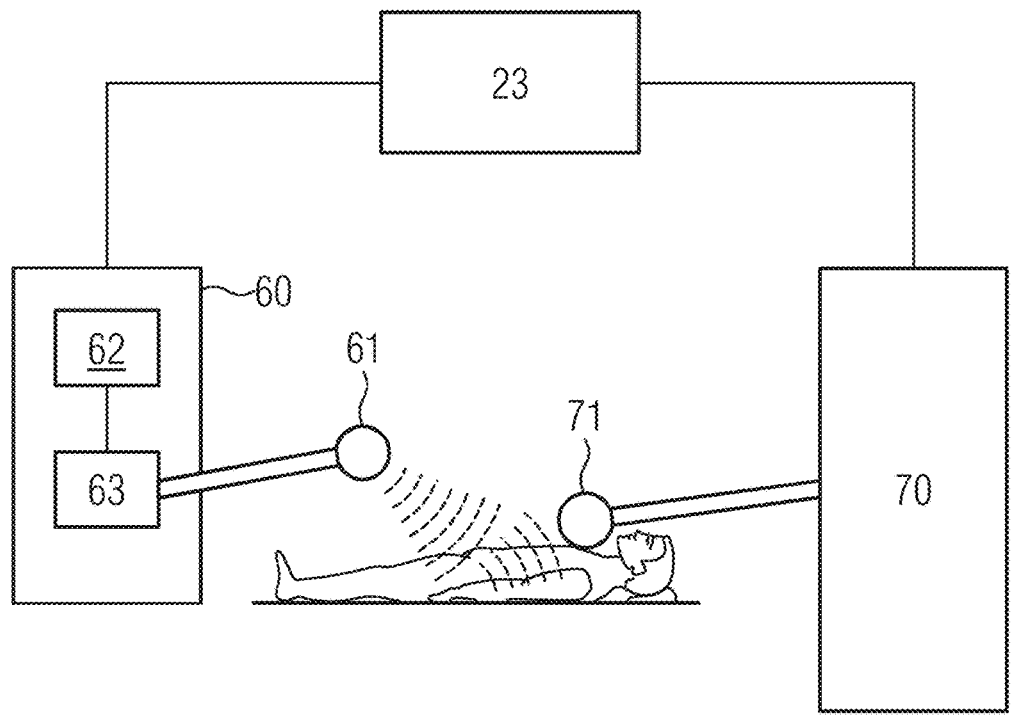
FIG. 2 shows a schematic of exemplary functional modules of a magnetic resonance tomography system provided for the pilot tone device.

In FIG. 2, the functional units required to acquire a physiological parameter using a pilot tone are shown schematically, based on which the functionality of the present embodiments is then to be explained. This may be the pilot tone devices shown in FIG. 1 in a magnetic resonance tomography system (1) of one or more of the present embodiments; it is, however, likewise conceivable for the pilot tone device shown by way of example in FIG. 2 to be autonomously realized without a magnetic resonance tomography system in a patient couch or as a wearable unit, for example.

The pilot tone transmitter 60 generates the pilot tone signal, which is then radiated into a patient via an induction loop 61. The pilot tone transmitter 60 has an oscillator 62 that generates a radio frequency signal with a suitable frequency. In one embodiment, the frequency in a magnetic resonance tomography system 1 as a medical image acquisition device is, for example, close to or in the frequency range of a Larmor frequency used by the magnetic resonance tomography system 1 during imaging. Instead of the oscillator 62 in the pilot tone transmitter 60, the radio frequency signal may be supplied by the radio frequency unit 22 (e.g., with a magnetic resonance tomography system 1) or generated from a supplied signal in the pilot tone transmitter in order to provide a sufficiently high frequency stability particularly with respect to the magnetic resonance signals and to minimize interactions with the image acquisition.

In another embodiment, the pilot tone transmitter 60 may use a frequency in another disjunct ISM band than the ISM band in which the frequency of the magnetic resonance signal lies.

The pilot tone device of one or more of the present embodiments with the pilot tone transmitter 60 and the pilot tone receiver 70 may also be carried out independently of a magnetic resonance tomography system 1 with separate components (e.g., in a patient couch 100 or in a mobile monitoring device). The use of a pilot tone signal in an ISM band is of particular advantage since even with conventional magnetic resonance tomography systems 1 with a radio frequency shielding chamber, the patient on the transport couch is able to leave this, and the pilot tone device may then adhere to the stricter emission regulations outside of the shielding chamber.

The pilot tone transmitter 60 also has a modulator 63 in order to modulate a modulation signal (e.g., a code generated by the modulator 63 on the radio frequency signal). Each code is essentially suited to allow a unique identification of the pilot tone signal. It is advantageous if the code has an item of phase information, so that in the receiver explained subsequently, a phase displacement is identified, and different propagation paths of the pilot tone signal may be differentiated. With a magnetic resonance tomography system 1, it is advantageous if the code generates as statistical a spectral distribution of the signal as possible in order to prevent image artifacts as a result of individual interfering peaks in the k-space. One possible way of generating such a code is a pseudo random sequence generator in the modulator 63, for example. Simple modulations with a sinusoidal signal (e.g., with a frequency of a few kHz) may also be provided, however.

The modulator 63 impresses the code or the modulation signal onto the radio frequency signal. Modulation methods such as amplitude modulation, frequency modulation, phase modulation, or more complex methods such as square amplitude modulation may be used, for example. A spread spectrum modulation may also be provided.

The pilot tone signal emitted by the induction coil 61 then extends in the patient tunnel 16 and impinges on different paths, partially through the patient, partially directly at the antenna coil 51. As a result of the absorption and phase shift, which change temporally with the physiological parameters and also as a result of the thus changing interference of waves of the pilot tone signal impinging on different propagation paths, a current that changes with the physiological parameters in terms of amplitude and/or phase is induced in the antenna coil 71. If the antenna coil 71 is one of several antenna coils (e.g., with a local coil 50 with an antenna matrix), the amplitude and/or phase of a number of spatially distributed locations may also be acquired and evaluated.

The signal of the antenna coil 71 is fed to the pilot tone receiver 70, which is typically firstly amplified and preprocessed (e.g., applies a band pass filter). A demodulation, complementary to the type of modulation used, then takes place. A decoding also takes place according to the coding used in the pilot tone transmitter 60. For a coding with a pseudo random sequence, a corresponding autocorrelation is carried out, with which the pilot tone signal is selected and an item of information relating to a phasing may also be determined. With scalar multiplication of the received signal with the template of the pseudo random sequence, the pilot tone signal is therefore separated with a correct phasing.

With an encoding by the frequency and/or phasing in the k-space, the pilot tone receiver may obtain an item of information from the controller 23 relating to the frequency and/or phase used by the pilot tone transmitter as a function of the trajectory or the pulse draw and select the corresponding signal with a filter in the k-space. In conjunction with a pseudo random sequence, an autocorrelation in the k-space may also be provided in order to select the pilot tone signal.

With a temporal encoding of the pilot tone signal, the pilot tone receiver 70 may suppress the input signal as a function of a signal of the controller 23 in synchrony with the pulse draw if the magnetic resonance signal is to be expected.

The pilot tone receiver 70 evaluates the pilot tone signal separated from the MR signals on the physiological parameters. Frequency-dependent and time-dependent filters may, for example, be used, and/or an adjustment (e.g., fitting) to predetermined measuring curves of comparable physiological processes may take place in order to extract a physiological parameter from the pilot tone signal. For example, different temporal curves of the pilot tone may be recorded while simultaneously measuring the breathing by chest belts or the heartbeat while simultaneously recording an EKG in order to subsequently also determine the physiological parameters such as point in time relative to the breathing cycle or heartbeat from the pilot signal by using artificial intelligence algorithms.

The pilot tone receiver 70 may be configured as a separate unit or as part of the image acquisition device. For example, with a magnetic resonance tomography system 1 with antennas and receivers of the radio frequency unit 22 and a pilot tone signal in the frequency range of the magnetic resonance signal, the receivers available to the MR signal may also be used for the pilot tone. With a digital signal processing, it the previously described filter and autocorrelation and decoding algorithms may be implemented as software on a signal processor or FPGA. In one embodiment, an algorithm for determining the physiological parameter may be carried out in the image evaluation or the controller 23.

In one embodiment of the pilot tone device, the pilot tone receiver 70 may perform an evaluation of a quality of the received pilot tone. For example, the pilot tone receiver 70 may have a detector for determining a signal-to-noise ratio (SNR) or also only a level meter for the pilot tone signal. The pilot tone receiver is configured to transmit an item of information relating to the thus determined quality of the pilot tone to the pilot tone transmitter 60 via a signal link. In one embodiment, the controller 23 may obtain and evaluate the information, and according to the result of the evaluation, the controller 23 may forward a control signal to the pilot tone transmitter 60 via the signal link. The pilot tone transmitter 60 has, for example, a radio frequency output stage with a control input, at which a stronger level signal or a corresponding control signal from the controller 23 reduces the emitted radio frequency power. The radiated radio frequency power is reduced to the required minimum or, in the case of the SNR, may also result, for example, in a power increase if the receive quality is too poor.

Other simple or complex analog and/or digital control loops, in which the emission of the pilot tone in the pilot tone transmitter 60 is influenced via evaluating the received pilot tone by the pilot tone receiver 70 may also be provided. For example, the controller 23 may be configured to perform this complex evaluation and to realize the control loop.

Although the invention has been illustrated and described in greater detail based on exemplary embodiments, the invention is not limited by the disclosed examples; other variations may be derived herefrom by the person skilled in the art without leaving the scope of protection of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A pilot tone device for acquiring physiological data, the pilot tone device comprising:
    a pilot tone transmitter configured to transmit a pilot tone in an ISM band; and
    a receiver configured to receive the pilot tone,
    wherein the pilot tone transmitter is configured to automatically set a transmit power of the pilot tone as a function of a disturbance level at a frequency of the pilot tone.

2. The pilot tone device of claim 1, wherein the pilot tone transmitter includes:
    a modulator configured to modulate the pilot tone with a correlation pattern; and
    a receiver that includes a correlator configured to filter the received pilot tone signal using the modulation.

3. A magnetic resonance tomography system comprising:
    a pilot tone device for acquiring physiological data, the pilot tone device comprising:

a pilot tone transmitter configured to transmit a pilot tone in a first ISM band,
wherein the magnetic resonance tomography system is configured to use a magnetic resonance signal in a second ISM band for imaging.

4. The magnetic resonance tomography system of claim 3, wherein the pilot tone transmitter and the magnetic resonance tomography system are configured to generate the pilot tone and the magnetic resonance signal in different ISM bands.

5. The magnetic resonance tomography system of claim 3, wherein the pilot tone transmitter and the magnetic resonance tomography system are configured to generate the pilot tone and the magnetic resonance signal in a same ISM band, and
wherein the pilot tone signal lies outside of a bandwidth of the magnetic resonance signal.

6. The magnetic resonance tomography system of claim 5, further comprising a receiver for the magnetic resonance signal,
wherein the receiver has a signal connection with the pilot tone transmitter and is configured to obtain a reference pilot tone signal from the pilot tone transmitter via a signal link, and the receiver is configured to suppress a portion of the pilot tone in a received magnetic resonance signal as a function of the reference pilot tone signal.

7. A pilot tone device for acquiring physiological data, the pilot tone device comprising:
a pilot tone transmitter configured to transmit a pilot tone in an ISM band, wherein the pilot tone transmitter includes:
a modulator configured to modulate the pilot tone with a correlation pattern; and
a receiver that includes a correlator configured to filter the received pilot tone signal using the modulation.

8. The pilot tone device of claim 7, further comprising:
a receiver configured to receive the pilot tone,
wherein the pilot tone transmitter is configured to set a transmit power of the pilot tone as a function of a disturbance level at a frequency of the pilot tone.

* * * * *